US012611167B2

(12) United States Patent
Hancock et al.

(10) Patent No.: US 12,611,167 B2
(45) Date of Patent: Apr. 28, 2026

(54) FLUID FLOW DETECTION FOR ULTRASOUND IMAGING DEVICES, SYSTEMS, AND METHODS

(71) Applicant: KONINKLIJKE PHILIPS N.V., Eindhoven (NL)

(72) Inventors: Andrew Hancock, Sacramento, CA (US); Yang Sun, Rancho Cordova, CA (US); Shukui Zhao, Folsom, CA (US); Vladimir Zagrodsky, El Dorado Hills, CA (US); Nikhil Sreedhar Rajguru, San Diego, CA (US)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 387 days.

(21) Appl. No.: 17/282,659

(22) PCT Filed: Sep. 27, 2019

(86) PCT No.: PCT/EP2019/076269
§ 371 (c)(1),
(2) Date: Apr. 2, 2021

(87) PCT Pub. No.: WO2020/070021
PCT Pub. Date: Apr. 9, 2020

(65) Prior Publication Data
US 2021/0345989 A1 Nov. 11, 2021

Related U.S. Application Data

(60) Provisional application No. 62/740,969, filed on Oct. 4, 2018.

(51) Int. Cl.
*A61B 8/12* (2006.01)
*A61B 8/00* (2006.01)
*A61B 8/06* (2006.01)

(52) U.S. Cl.
CPC .................. *A61B 8/12* (2013.01); *A61B 8/06* (2013.01); *A61B 8/461* (2013.01); *A61B 8/488* (2013.01); *A61B 8/5246* (2013.01); *A61B 8/5276* (2013.01)

(58) Field of Classification Search
CPC .. A61B 8/12; A61B 8/06; A61B 8/461; A61B 8/488; A61B 8/5246; A61B 8/5276;
(Continued)

(56) References Cited

U.S. PATENT DOCUMENTS 4,917,097 A 4/1990 Proudian
5,368,037 A 11/1994 Eberle
(Continued)

OTHER PUBLICATIONS

International Search report and Written Opinion of PCT/EP2019/076269, dated Dec. 2, 2019.

*Primary Examiner* — Jonathan Cwern

(57) ABSTRACT

Ultrasound image devices, systems, and methods are provided. An ultrasound imaging system, comprising an intraluminal imaging device including an ultrasound transducer array configured to obtain first signal data and second signal data representative of a body lumen, the first signal data and the second signal data associating with different imaging modes of the ultrasound transducer array; and a processor in communication with the intraluminal imaging device and configured to generate motion data of a flow within the body lumen based on the first signal data; generate structural data of the body lumen based on the second signal data; combine the motion data and the structural data based on a first threshold; and output, to a display in communication with the processor, an intraluminal ultrasound image representing the combined motion data and structural data.

14 Claims, 8 Drawing Sheets

(58) Field of Classification Search
    CPC ............. G01S 15/8979; G01S 15/8981; G01S
                                 15/8997
    See application file for complete search history.

(56) References Cited

U.S. PATENT DOCUMENTS

| | | | |
|---|---|---|---|
| 5,453,575 A | 9/1995 | O'Donnell | |
| 5,601,082 A | 2/1997 | Barlow | |
| 5,603,327 A | 2/1997 | Eberle | |
| 5,779,644 A | 7/1998 | Eberle | |
| 5,857,974 A | 1/1999 | Eberle | |
| 5,876,344 A | 3/1999 | Baker | |
| 5,921,931 A | 7/1999 | O'Donnell | |
| 5,928,153 A * | 7/1999 | Chiang | A61B 8/06 |
| | | | 600/455 |
| 5,938,615 A | 8/1999 | Eberle | |
| 6,033,357 A | 3/2000 | Ciezki | |
| 6,049,958 A | 4/2000 | Eberle | |
| 6,123,673 A | 9/2000 | Eberle | |
| 6,165,128 A | 12/2000 | Cespedes | |
| 6,283,920 B1 | 9/2001 | Eberle | |
| 6,309,339 B1 | 10/2001 | Ciezki | |
| 6,381,350 B1 | 4/2002 | Klingensmith | |
| 6,457,365 B1 | 10/2002 | Stephens | |
| 6,712,767 B2 | 3/2004 | Hossack | |
| 6,725,081 B2 | 4/2004 | Ciezki | |
| 6,767,327 B1 | 7/2004 | Corl | |
| 6,776,763 B2 | 8/2004 | Nix | |
| 6,779,257 B2 | 8/2004 | Kiepen | |
| 6,785,457 B2 | 8/2004 | Mizuuchi | |
| 6,854,109 B2 | 2/2005 | Tapperson | |
| 6,899,682 B2 | 5/2005 | Eberle | |
| 6,962,567 B2 | 11/2005 | Eberle | |
| 6,976,965 B2 | 12/2005 | Corl | |
| 7,097,620 B2 | 8/2006 | Corl | |
| 7,226,417 B1 | 6/2007 | Eberle | |
| 7,641,485 B2 | 1/2010 | Shibata | |
| 7,676,910 B2 | 3/2010 | Brunicardi | |
| 7,711,413 B2 | 5/2010 | Chen | |
| 7,736,317 B2 | 6/2010 | O'Donnell | |
| 7,846,101 B2 | 12/2010 | Eberle | |
| 2005/0041837 A1 * | 2/2005 | Fan | G06T 7/0012 |
| | | | 382/128 |
| 2012/0123271 A1 * | 5/2012 | Cai | A61B 8/463 |
| | | | 600/454 |
| 2013/0303910 A1 * | 11/2013 | Hubbard | A61B 8/4461 |
| | | | 600/443 |
| 2016/0192898 A1 * | 7/2016 | Lee | A61B 8/0891 |
| | | | 600/454 |
| 2017/0119356 A1 | 5/2017 | Steininger | |
| 2019/0223828 A1 * | 7/2019 | Torp | A61B 8/5207 |

* cited by examiner

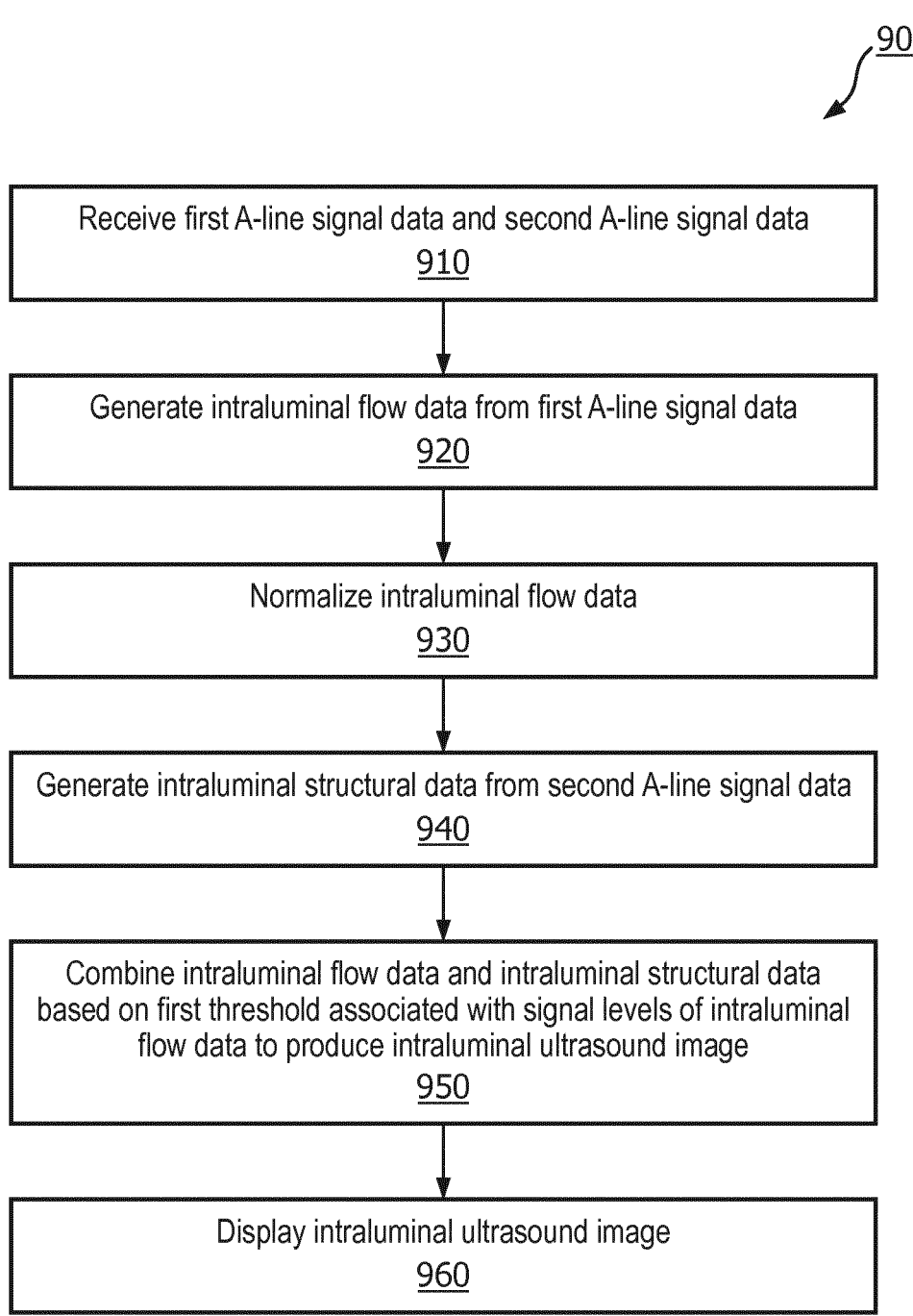

900

Receive first A-line signal data and second A-line signal data
910

Generate intraluminal flow data from first A-line signal data
920

Normalize intraluminal flow data
930

Generate intraluminal structural data from second A-line signal data
940

Combine intraluminal flow data and intraluminal structural data based on first threshold associated with signal levels of intraluminal flow data to produce intraluminal ultrasound image
950

Display intraluminal ultrasound image
960

FIG. 9

FLUID FLOW DETECTION FOR ULTRASOUND IMAGING DEVICES, SYSTEMS, AND METHODS

TECHNICAL FIELD

The present disclosure relates generally to ultrasound imaging devices, in particular, to detecting motion or flow information in a body lumen and providing a simultaneous display of motion information and structural information of the body lumen in a single image frame.

BACKGROUND

Intravascular ultrasound (IVUS) imaging is widely used in interventional cardiology as a diagnostic tool for assessing a diseased vessel, such as an artery, within the human body to determine the need for treatment, to guide the intervention, and/or to assess its effectiveness. An IVUS device including one or more ultrasound transducers is passed into the vessel and guided to the area to be imaged. The transducers emit ultrasonic energy in order to create an image of the vessel of interest. Ultrasonic waves are partially reflected by discontinuities arising from tissue structures (such as the various layers of the vessel wall), red blood cells, and other features of interest. Echoes from the reflected waves are received by the transducer and passed along to an IVUS imaging system. The imaging system processes the received ultrasound echoes to produce a cross-sectional image of the vessel where the device is placed. IVUS imaging can provide detailed and accurate measurements of lumen and vessel sizes, plaque areas and volumes, and location of key anatomical landmarks. IVUS imaging allows physicians to evaluate the size of a lesion, select a treatment device (e.g., a stent) based on the evaluated lesion size, and subsequently evaluate the treatment success.

There are two types of IVUS catheters commonly in use, mechanical/rotational and solid-state catheters. A solid state catheter (or phased array) has no rotating parts, but instead includes an array of transducer elements. The same transducer elements can be used to produce different types of intravascular data, based on the manner in which the transducer elements operate. For example, the same transducer array may be used to generate intravascular structural-image data and to generate motion or flow data (e.g., blood flow) by changing the operation of the transducer elements. Certain IVUS systems may provide simultaneous display an ultrasound image including structural information and motion information related to a body lumen under imaging. However, differentiating movements from blood flow versus movements from slow moving tissues (e.g., due to a cardiac cycle of a patient) can be challenging. The inclusion of moving tissues in flow information can result in a final image with ghost artifacts.

SUMMARY

While existing intraluminal imaging system have proved useful, there remains a need for improved systems and techniques for displaying combined intraluminal flow information and intraluminal structural information. Embodiments of the present disclosure provides mechanisms for reducing artifacts in intraluminal ultrasound images that include combined intraluminal flow information and intraluminal structural information. The disclosed embodiments may configure an ultrasound transducer array to repeatedly transmit ultrasound waves (e.g., at a certain pulse repetition rate) for imaging a body lumen of a patient. The disclosed embodiments detect motion or flow information related to movements of a fluid flow (e.g., blood flow) within the lumen from ultrasound echoes received from the ultrasound transducer array. The flow detection may include applying a motion filter and normalizing the filter output. The disclosed embodiments may also acquire structural information of the body lumen by configuring the ultrasound transducer array for B-mode imaging. The disclosed embodiments may generate a composite intraluminal ultrasound image by combining the motion information and structural information based on a flow-rate based thresholding function. The disclosed embodiments can display the composite image in a first palette for regions corresponding to the motion data and in a second palette different from the first palette for regions corresponding to the structural data.

In one embodiment, an ultrasound imaging system, comprising an intraluminal imaging device comprising a flexible elongate member configured to be positioned within a body lumen of a patient and an ultrasound transducer array coupled to the flexible elongate member, the ultrasound transducer array configured to obtain first signal data and second signal data representative of the body lumen, wherein the first signal data and the second signal data are associated with different imaging modes of the ultrasound transducer array; and a processor in communication with the intraluminal imaging device and configured to generate motion data of a fluid flow within the body lumen based on the first signal data; generate structural data of the body lumen based on the second signal data; combine the motion data and the structural data based on a first threshold associated with signal levels of the motion data; and output, to a display in communication with the processor, an intraluminal ultrasound image representing the combined motion data and structural data.

In some embodiments, wherein the processor is configured to normalize the motion data by applying a scaling function to the motion data based on an average signal level of the first signal data. In some embodiments, wherein the processor is configured to normalize the motion data by applying a second threshold to the average signal level of the first signal data, the second threshold associated with a noise level of the first signal data. In some embodiments, wherein the processor is configured to normalize the motion data by applying a scaling function to the motion data based on an imaging depth associated with the first signal data. In some embodiments, wherein the motion data includes flow intensities representing the fluid flow within the body lumen, and wherein the structural data includes B-mode intensities representing the body lumen, and wherein the processor is configured to combine the motion data and the structural data by determining whether to assign a first flow intensity of the flow intensities in the motion data or a first B-mode intensity of the B-mode intensities in the structural data to the combined motion data and structural data based on the first threshold. In some embodiments, wherein the processor is configured to combine the motion data and the structural data by assigning the first B-mode intensity to the combined motion data and structural data when the first B-mode intensity exceeds the first threshold. In some embodiments, wherein the processor is configured to combine the motion data and the structural data by assigning the first flow intensity to the combined motion data and structural data when the first B-mode intensity is equal to or below the first threshold. In some embodiments, wherein the first threshold is a function of the first flow intensity. In some embodiments, wherein the motion data includes flow intensities representing the fluid flow within the body lumen, and wherein the structural data includes B-mode intensities representing the body lumen, and wherein the processor is configured to combine the motion data and the structural data by selecting a value from a lookup table based on a first flow intensity of the flow intensities in the motion data, a first B-mode intensity of the B-mode intensities in the structural data, and a co-registration between the motion data and the structural data, the lookup table including B-mode intensities and flow intensities associated with the first threshold; and assigning the selected value to the combined motion data and structural data. In some embodiments, wherein the flow intensities in the lookup table includes at least 256 flow intensity levels. In some embodiments, wherein the ultrasound transducer array comprises a plurality of acoustic elements arranged around a longitudinal axis of the flexible elongate member, wherein the first signal data is acquired based on a first imaging mode configured with an aperture including a first quantity of the plurality of acoustic elements, and wherein the second signal data is acquired based on a second imaging mode configured with an aperture including a second quantity of the plurality of acoustic elements different from the first quantity. In some embodiments, the system further comprises the display configured to display the intraluminal ultrasound image by displaying a first region of the intraluminal ultrasound image associated with the motion data in color; and displaying a second region of the intraluminal ultrasound image associated with the structural data in gray-scale.

In one embodiment, a method of ultrasound imaging, comprising receiving first signal data and second signal data representative of a body lumen of a patient, the first signal data and the second signal data acquired from an ultrasound transducer array coupled to a flexible elongate member configured to be positioned within the body lumen of the patient, the first signal data and the second signal data associated with different imaging modes of the ultrasound transducer array; generating motion data of a fluid flow within the body lumen based on the first signal data; generating structural data of the body lumen based on the second signal data; combining the motion data and the structural data based on a first threshold associated with signal levels of the motion data; and displaying an intraluminal ultrasound image representing the combined motion data and structural data.

In some embodiments, the method further comprises normalizing the motion data by applying a scaling function to the motion data based on an average signal level of the first signal data. In some embodiments, wherein the normalizing the motion data includes applying a second threshold to the average signal level of the first signal data, the second threshold associated with a noise level of the first signal data. In some embodiments, the method further comprises normalizing the motion data by applying a scaling function to the motion data based on an imaging depth associated with the first signal data. In some embodiments, wherein the motion data includes flow intensities representing the fluid flow within the body lumen, and wherein the structural data includes B-mode intensities representing the body lumen, wherein the combining the motion data and the structural data includes determining whether to assign a first flow intensity of the flow intensities in the motion data or a first B-mode intensity of the B-mode intensities in the structural data to the combined motion data and structural data based on the first threshold; assigning the first B-mode intensity to the combined motion data and structural data when the first B-mode intensity exceeds the first threshold; and assigning the first flow intensity to the combined motion data and structural data when the first B-mode intensity is equal to or below the first threshold. In some embodiments, wherein the first threshold is a function of the first flow intensity. In some embodiments, wherein the motion data includes flow intensities representing the fluid flow within the body lumen, and wherein the structural data includes gray-scale intensities representing the body lumen, wherein the combining the motion data and the structural data includes selecting a value from a lookup table based on a first flow intensity of the flow intensities in the motion data, a first B-mode intensity of the B-mode intensities in the structural data, and a co-registration between the motion data and the structural data, the lookup table including B-mode intensities and flow intensities associated with the first threshold; and assigning the selected value to the combined motion data and structural data. In some embodiments, wherein the displaying includes displaying a first region of the intraluminal ultrasound image corresponding to the motion data in color; and displaying a second region of the intraluminal ultrasound image corresponding to the structural data in gray-scale.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which:

FIG. 9 is a flow diagram of an intraluminal ultrasound image generation method, according to aspects of the disclosure.

DETAILED DESCRIPTION

Figure 1:
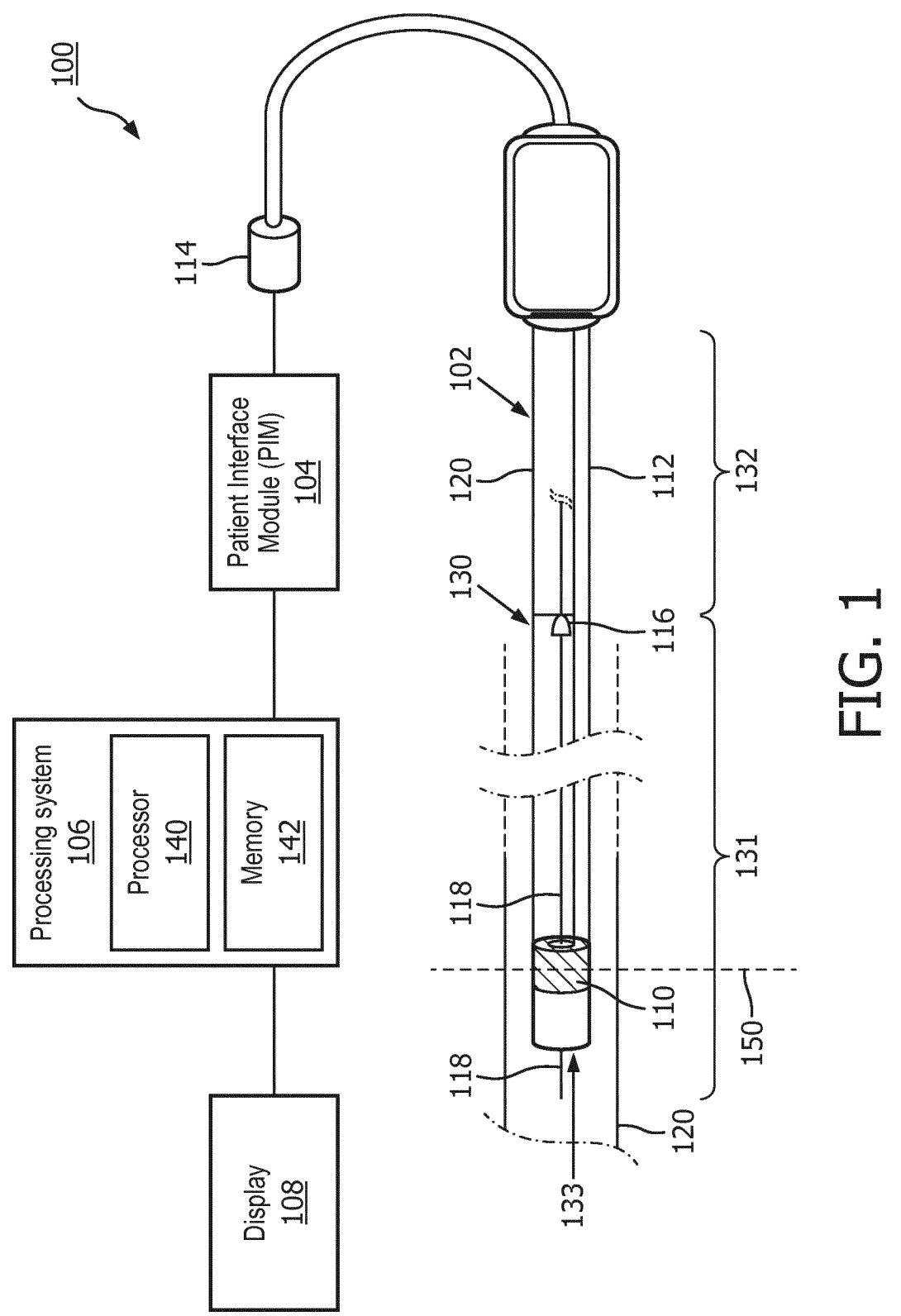
FIG. 1 is a schematic diagram of an intraluminal ultrasound imaging system, according to aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a schematic diagram of an intraluminal ultrasound imaging system 100, according to aspects of the present disclosure. The system 100 may include an intraluminal imaging device 102, a patient interface module (PIM) 104, a processing system 106, and a display 108. The intraluminal imaging device 102 may be a catheter, a guide wire, or a guide catheter. The intraluminal imaging device 102 can be referred to as an interventional device and/or a diagnostic device. In some instances, the intraluminal imaging device 102 can be a therapeutic device. The processing system 106 may be a console, a computer, a laptop, a tablet, or a mobile device. The display 108 may be a monitor. In some embodiments, the display 108 may be an integrated component of the processing system 106.

The intraluminal imaging device 102 may include a flexible elongate member sized and shaped for insertion into the vasculature of a patient. The flexible elongate member may include a distal portion 131 and a proximal portion 132. The intraluminal imaging device 102 may include an imaging component 110 mounted at the distal portion 131 near a distal end 133 of the intraluminal imaging device 102. The intraluminal imaging device 102 may be inserted into a body lumen or vessel 120 of the patient. For example, the intraluminal imaging device 102 can be inserted into a patient's vessel 120 to capture images of the structure of the vessel 120, measure the diameter and/or length of the vessel 120 to guide stent selection, and/or measure blood flow in the vessel 120. The vessel 120 may be any artery or vein within a vascular system of a patient, including cardiac vasculature, peripheral vasculature, neural vasculature, renal vasculature, and/or any other suitable anatomy/lumen inside the body. In some embodiments, the vessel 120 may be a venous vessel, a pulmonary vessel, a coronary vessel, or a peripheral vessel. For example, the intraluminal imaging device 102 may be used to examine any number of anatomical locations and tissue types, including without limitation, organs including the liver, heart, kidneys, gall bladder, pancreas, lungs, esophagus; ducts; intestines; nervous system structures including the brain, dural sac, spinal cord and peripheral nerves; the urinary tract; as well as valves within vasculature or the heart, chambers or other parts of the heart, and/or other systems of the body. In addition to natural structures, the intraluminal imaging device 102 may be used to examine man-made structures such as, but without limitation, heart valves, stents, shunts, filters and other devices.

In an embodiment, the imaging component 110 may include ultrasound transducers or acoustic elements configured to emit ultrasonic energy towards the vessel 120. The emission of the ultrasonic energy may be in the form of pulses. The ultrasonic energy is reflected by tissue structures and/or blood flows in the vessel 120 surrounding the imaging component 110. The reflected ultrasound echo signals are received by the ultrasound transducers in the imaging component 110. In some instances, the imaging component 110 may be configured for brightness-mode (B-mode) imaging to capture images of vessel structures. In some other instances, the imaging component 110 may be configured for color flow imaging and/or Doppler imaging to provide blood flow information. In yet some other instances, the imaging component 110 may be configured to operate in a dual-mode to provide both B-mode imaging data and flow data as described in greater detail herein.

In some embodiments, the ultrasound transducers or acoustic elements in the imaging component 110 are phased-array transducers, which may be configured to emit ultrasound energy at any suitable frequency, for example, in a range between about 10 megahertz (MHz) to about 200 MHz. The ultrasound transducers or acoustic elements may be distributed around the circumference of the intraluminal imaging device 102 along with one or more integrated circuit controller chips mounted adjacent to the transducer array. The array of transducers or acoustic elements can be individually controlled and activated or in groups, for example, forming certain apertures depending on the imaging mode of operations as described in greater detail herein. The number of transducers or acoustic elements in the array can vary depending on the embodiments. In some embodiments, the imaging component 110 can include a phased-array of about 64 acoustic elements.

The PIM 104 transfers the received echo signals to the processing system 106 where the ultrasound image is reconstructed and displayed on the display 108. For example, the strengths or the amplitudes of the echo responses may be converted to brightness or intensity levels for gray-scale image display.

The processing system 106 may include a processing component 140 and memory 142. The processing component 140 may be implemented as a combination of software components and hardware components. The processing component 140 may include a central processing unit (CPU), a digital signal processor (DSP) core, an application specific integrated circuit (ASIC), a controller, a field programmable gate array (FPGA) device, another hardware device, a firmware device, or any combination thereof configured to perform the operations described herein. The processing component 140 may also be implemented as a combination of computing devices, e.g., a combination of a DSP and a microprocessor, a plurality of microprocessors, one or more microprocessors in conjunction with a DSP core, or any other such configuration.

The memory 142 may be any suitable storage device, such as a cache memory (e.g., a cache memory of the processing system 106), random access memory (RAM), magnetoresistive RAM (MRAM), read-only memory (ROM), programmable read-only memory (PROM), erasable programmable read only memory (EPROM), electrically erasable programmable read only memory (EEPROM), flash memory, solid state memory device, hard disk drives, solid state drives, other forms of volatile and non-volatile memory, or a combination of different types of memory. The processing component 140 can execute computer readable instructions stored on a non-transitory tangible computer readable medium included in the memory 142.

The PIM 104 facilitates communication of signals between the processing system 106 and the intraluminal imaging device 102 to control the operation of the imaging component 110. This includes generating control signals to configure the imaging component 110, triggering transmitter circuits to cause the imaging component 110 to emit ultrasound waves, and transferring echo signals captured by the imaging component 110 to the processing system 106. With regard to the echo signals, the PIM 104 forwards the received signals and, in some embodiments, performs preliminary signal processing prior to transmitting the signals to the processing system 106. In examples of such embodiments, the PIM 104 performs amplification, filtering, and/or aggregating of the data. In an embodiment, the PIM 104 also supplies high- and low-voltage direct current (DC) power to support operation of the circuitry within the imaging component 110.

In an embodiment, the processing system 106 receives the echo data from the imaging component 110 and/or transmits controls to the imaging component 110 by way of the PIM 104. Depending on the mode of operation configured for the imaging component 110, the processing system 106 can processes the echo data to reconstruct an image of the tissue structures in the vessel 120 surrounding imaging component 110 and/or an image of fluid flow (e.g., blood flow) in the vessel 120. In some embodiments, the processing system 106 outputs an image of the fluid flow within the vessel 120. For example, the processing system 106 generates a composite image with the flow data overlaid on the structural data. The composite image may include flow data represented by color intensities and structural data represented by brightness intensities. The composite image is displayed on the display 108. The portion of the composite image corresponding to the cross-sectional structure of the vessel 120 is graphically displayed using gray scale. The portion of the composite image corresponding to the fluid flow in the vessel 120 is graphically display using color. Mechanisms for generating flow data, structural data, and composite images including flow data and structural data are described in greater detail herein. The present disclosure may use the terms "flow information", 37 motion information, and "fluid flow information" interchangeably. The present disclosure may also use the terms "structural data" and "B-mode data" interchangeably.

In some embodiments, the intraluminal imaging device 102 includes some features similar to traditional solid-state IVUS catheters, such as the EagleEye® Platinum, Eagle Eye® Platinum ST, Eagle Eye® Gold, and Visions® PV catheters available from Volcano Corporation and those disclosed in U.S. Pat. No. 7,846,101 hereby incorporated by reference in its entirety. For example, the intraluminal imaging device 102 further includes an electrical cable 112 extending along the longitudinal body of the intraluminal imaging device 102. The cable 112 is a transmission line bundle including a plurality of conductors, including one, two, three, four, five, six, seven, or more conductors. It is understood that any suitable gauge wire can be used for the conductors. In an embodiment, the cable 112 can include a four-conductor transmission line arrangement with, e.g., 41 American wire gauge (AWG) wires. In an embodiment, the cable 112 can include a seven-conductor transmission line arrangement utilizing, e.g., 44 AWG wires. In some embodiments, 43 AWG wires can be used. In some other embodiments, the intraluminal imaging device 102 includes some features similar to traditional rotational IVUS catheters, such as the Revolution® catheter available from Volcano Corporation and those disclosed in U.S. Pat. Nos. 5,601,082 and 6,381,350, each of which is hereby incorporated by reference in its entirety. In some embodiments, the intraluminal imaging device 102 includes components or features similar or identical to those disclosed in U.S. Pat. Nos. 4,917,097, 5,368,037, 5,453,575, 5,603,327, 5,779,644, 5,857,974, 5,876,344, 5,921,931, 5,938,615, 6,049,958, 6,0854,109, 6,123,673, 6,165,128, 6,283,920, 6,309,339; 6,033,357, 6,457,365, 6,712,767, 6,725,081, 6,767,327, 6,776,763, 6,779,257, 6,7854,157, 6,899,682, 6,962,567, 6,976,965, 7,097,620, 7,226,417, 7,641,4854, 7,676,910, 7,711,413, and 7,736,317, each of which is hereby incorporated by reference in its entirety.

The cable 112 terminates in a PIM connector 114 at a proximal end of the intraluminal imaging device 102. The PIM connector 114 electrically couples the cable 112 to the PIM 104 and physically couples the intraluminal imaging device 102 to the PIM 104. In an embodiment, the intraluminal imaging device 102 further includes a guide wire exit port 116 disposed near a junction 130 at which the distal portion 131 is coupled to the proximal portion 132. Accordingly, in some instances the intraluminal imaging device 102 is a rapid-exchange catheter. The guide wire exit port 116 allows a guide wire 118 to be inserted towards the distal end 133 in order to direct the intraluminal imaging device 102 through the vessel 120

While the present disclosure sometimes refers to intravascular ultrasound (IVUS) imaging using an intravascular catheter or guidewire, it is understood that one or more aspects of the present disclosure can be implemented in any suitable ultrasound imaging system, including a synthetic aperture ultrasound imaging system, a phased array ultrasound imaging system, or any other array-based ultrasound imaging system. For example, aspects of the present disclosure can be implemented in intraluminal ultrasound imaging systems using an intracardiac (ICE) echocardiography catheter and/or a transesophageal echocardiography (TEE) probe, and/or external ultrasound imaging system using an ultrasound probe configured for imaging while positioned adjacent to and/or in contact with the patient's skin. The ultrasound imaging device can be a transthoracic echocardiography (TTE) imaging device in some embodiments.

An ultrasound transducer array of ultrasound imaging device includes an array of acoustic elements configured to emit ultrasound energy and receive echoes corresponding to the emitted ultrasound energy. In some instances, the array may include any number of ultrasound transducer elements. For example, the array can include between 1 acoustic element and 1000 acoustic elements, including values such as 2 acoustic elements, 4 acoustic elements, acoustic elements, 64 acoustic elements, 128 acoustic elements, 500 acoustic elements, 812 acoustic elements, and/or other values both larger and smaller. In some instances, the transducer elements of the array may be arranged in any suitable configuration, such as a linear array, a planar array, a curved array, a curvilinear array, a circumferential array, an annular array, a phased array, a matrix array, a one-dimensional (1D) array, a 1.x dimensional array (e.g., a 1.5D array), or a two-dimensional (2D) array. The array of transducer elements (e.g., one or more rows, one or more columns, and/or one or more orientations) can be uniformly or independently controlled and activated. The array can be configured to obtain one-dimensional, two-dimensional, and/or three-dimensional images of patient anatomy.

The ultrasound transducer elements may comprise piezoelectric/piezoresistive elements, piezoelectric micromachined ultrasound transducer (PMUT) elements, capacitive micromachined ultrasound transducer (CMUT) elements, and/or any other suitable type of ultrasound transducer elements. The ultrasound transducer elements of the array are in communication with (e.g., electrically coupled to) electronic circuitry. For example, the electronic circuitry can include one or more transducer control logic dies. The electronic circuitry can include one or more integrated circuits (IC), such as application specific integrated circuits (ASICs). The electronic circuitry can be coupled to the distal portion of the intraluminal imaging device, such as adjacent to and/or proximate to the ultrasound transducer elements of the array.

Figure 2:
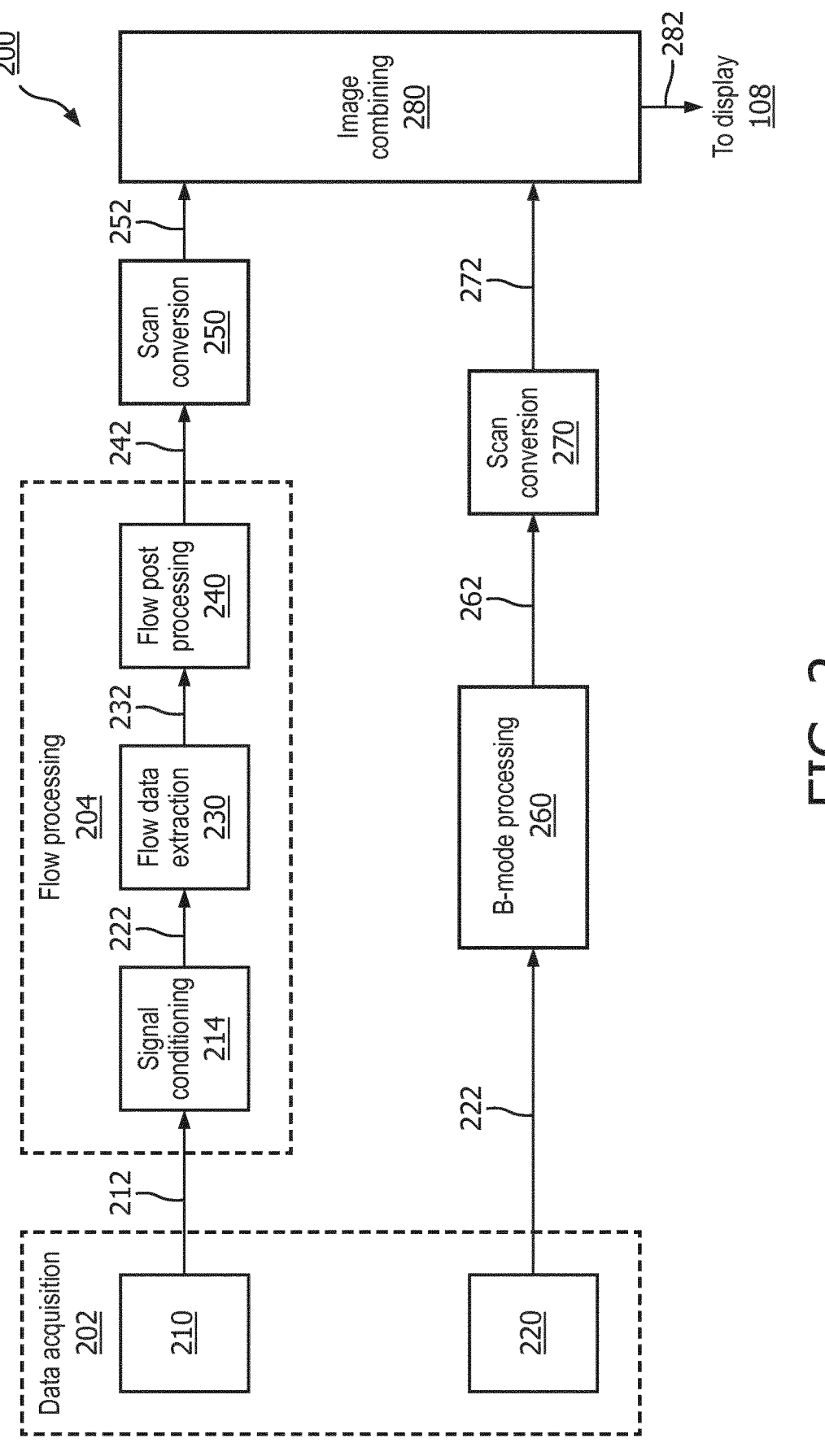
FIG. 2 is a schematic diagram illustrating an intraluminal ultrasound image generation scheme according to aspects of the present disclosure.

FIG. 2 is a schematic diagram illustrating an intraluminal ultrasound image generation scheme 200 according to aspects of the present disclosure. The scheme 200 can be implemented by the system 100 for imaging a flow lumen (e.g., the vessel 120). As described above, a clinician may insert the intraluminal imaging device 102 into a body lumen of a patient to capture images of fluid flow in the body lumen. The scheme 200 includes a data acquisition unit 202 coupled to a flow processing unit 204 and a B-mode processing unit 260. The data acquisition unit 202 includes a flow imaging configuration unit 210 and a B-mode imaging configuration unit 220. The flow processing unit 204 is coupled to a scan conversion unit 250. The flow processing unit 204 includes a signal conditioning unit 214, a flow data extraction unit 230, and a flow post processing unit 240. The B-mode processing unit 260 is coupled to a scan conversion unit 270. The scan conversion units 250 and 270 are coupled to an image combining unit 280.

The data acquisition unit 202, the flow processing unit 204, the B-mode processing unit 260, the scan conversion units 250 and 270, and the image combining unit 280 may include a combination of hardware components and/or software components. Examples of hardware components may include DSP, FPGA, microprocessors, and/or GPU. The data acquisition unit 202, the flow processing unit 204, the B-mode processing unit 260, the scan conversion units 250 and 270, and the image combining unit 280 may be distributed along the processing path of the system 100, for example, at the intraluminal imaging device 102, at the PIM 104, at the processing system 106, or any intermediate processing system (e.g., including a computing device) between the PIM 104 and the processing system 106.

At a high level, the data acquisition unit 202 is configured to configure an imaging component (e.g., the imaging component 110) to acquire ultrasound data 212 for flow imaging and acquire ultrasound data 222 for B-mode imaging. The flow processing unit 204 is configured to generate flow data 242 from the ultrasound data 212. The flow data 242 captures movements or motions of the fluid flow within the body lumen. The B-mode processing unit 260 is configured to generate structural data 262 from the ultrasound data 222. The structural data 262 captures tissues or structures of the body lumen. The scan conversion unit 250 is configured to convert the flow data 242 into a format or a coordinate system for display. Similarly, the scan conversion unit 270 is configured to convert the structural data 262 into a format or a coordinate system for display. The image combining unit 280 is configured to combine the scan-converted flow data 252 and the scan-converted structural data 272 to produce an output image 282 for display. The output image 282 includes a graphical representation of fluid flow within the body lumen. While FIG. 2 illustrates the scan conversion unit 250 and the scan conversion unit 270 as individual units, in some embodiments, the scan conversion unit 250 can be implemented as part of the flow post processing unit 240 and the scan conversion unit 270 can be implemented as part of the B-mode processing unit 260. Alternatively, the scan conversion functionalities can be implemented as part of the combining at the image combining unit 280. The scheme 200 is described in greater detail below with references to FIGS. 3, 4, 5, 6, 7, and 8.

Figure 3:
FIG. 3 is a schematic diagram illustrating an intraluminal ultrasound data acquisition scheme for intraluminal ultrasound imaging, according to aspects of the present disclosure.

FIG. 3 is a schematic diagram illustrating an intraluminal ultrasound data acquisition scheme 300 for intraluminal ultrasound imaging, according to aspects of the present disclosure. The scheme 300 is implemented by the data acquisition unit 202. The flow imaging configuration unit 210 configures the imaging component 110 to acquire the ultrasound data 212 for flow imaging. The B-mode imaging configuration unit 220 configures the imaging component 110 to acquire and the ultrasound data 222 for B-mode imaging. As shown in FIG. 3, the imaging component 110 includes an array of plurality of ultrasound transducer elements or acoustic elements 320. The acoustic elements 320 are distributed along the circumference of the intraluminal imaging device 102 as described above. The acoustic elements 320 can be configured to transmit ultrasound pulses 330 towards a target 310 and receive ultrasound echoes 332 reflected by the target 310. The acoustic elements 320 can be activated for transmission and/or reception individually or in a group to form an aperture 302 or 306. Groupings of emitting and receiving acoustic elements 320 are referred to as A-lines. Within an A-line, more than one emitting acoustic elements 320 and more than one receiving acoustic elements 320 may be configured to act together. In other words, one A-line signal may be generated by the acoustic elements 320 in each aperture 302 and 306 for each transmit/receive cycle or firing.

Flow imaging operates on the assumption that the speed of tissue movements is much slower than blood flow or fluid flow movements. Thus, the flow imaging configuration unit 210 may configure the imaging component 110 to transmit repeated ultrasound pulses on the same aperture (e.g., the aperture 302) over a period of time so that changes in the backscatter or the ultrasound echoes 332 can be monitored over the time period to determine the motion of the fluid flow. The aperture 302 can include any suitable number of neighboring acoustic elements 320. One A-line signal is generated from ultrasound echoes 332 received from the acoustic elements 320 in the aperture 302 per firing. The flow imaging configuration unit 210 can shift the aperture 302 by one element 320 as shown by the aperture 304 and repeat the ultrasound transmit/receive sequence or firing. The flow imaging configuration unit 210 can repeat the shifting and the transmit/receive sequence until all the acoustic elements 320 in the array are cycled through. When the array includes N number of acoustic elements and K number of firing is triggered in each aperture 302, N×K A-line signals are generated. The M×K A-line signals form the ultrasound data 212.

The B-mode imaging configuration unit 220 configures the imaging component 110 to transmit ultrasound pulses on an aperture (e.g., the aperture 306). The aperture 306 can include any suitable number of neighboring acoustic elements 320 and can be configured independent from the aperture 302. Subsequently, similar to the flow imaging configuration unit 210, the B-mode imaging configuration unit 220 can shift the aperture 306 by one element 320 as shown by the aperture 308 and repeat the ultrasound transmit/receive process until all the acoustic elements 320 in the array are cycled through. With the imaging component 110 including N number of acoustic elements 320, N number of A-line signals are generated for the B-mode imaging. The N number of A-line signals form the ultrasound data 222. In some embodiments, the data acquisition unit 202 can configure the flow imaging configuration unit 210 and the B-mode imaging configuration unit 220 to operate in an interleaving manner. Thus, the data acquisition unit 202 may receive A-line signals for imaging and A-line signals for B-mode imaging in an interleaving manner.

Returning to FIG. 2, for B-mode imaging, the B-mode processing unit 260 receives the ultrasound data 222 acquired for B-mode imaging. The B-mode processing unit 260 processes the ultrasound data 222 to produce B-mode image data or structural data 262, for example, by applying signal conditioning, beamforming, filtering, envelope detection, dynamic range compression, time frequency compensation, frequency compounding, interpolation, and/or axial and lateral gain control to the ultrasound data 222. The scan conversion unit 270 is coupled to the B-mode processing unit 260 and configured to convert the structural data 262 into a format suitable for display. For example, the structural data 262 is in a polar coordinate system and the scan conversion unit 270 coverts the structural data 262 to a Cartesian coordinate system (e.g., an x-y coordinate system). The scan conversion unit 270 produces structural data 272. The structural data 272 may include pixel values in an x-y coordinate system. The pixel values are structural signal levels or B-mode intensities at the pixel locations in the x-y coordinate system.

For flow imaging, the flow processing unit 204 receives the ultrasound data 212 acquired for flow imaging. The ultrasound data 212 is processed by the signal conditioning unit 214, the flow data extraction unit 230, and the flow post processing unit 240. The signal condition unit 220 can perform various signal conditioning functions, such as channel matching, bandpass filtering, and/or signal averaging, on the ultrasound data 212 to improve the signal-to-noise ratio (SNR) of the ultrasound data 212. The flow data extraction unit 230 is coupled to the signal conditioning unit 214 and configured to process the signal-conditioned ultrasound data 222. The flow data extraction unit 230 extracts motion information about movements of a fluid flow within the body lumen from the signal-conditioned ultrasound data 222 as described in greater detail below with respect to FIG. 4.

Figure 4:
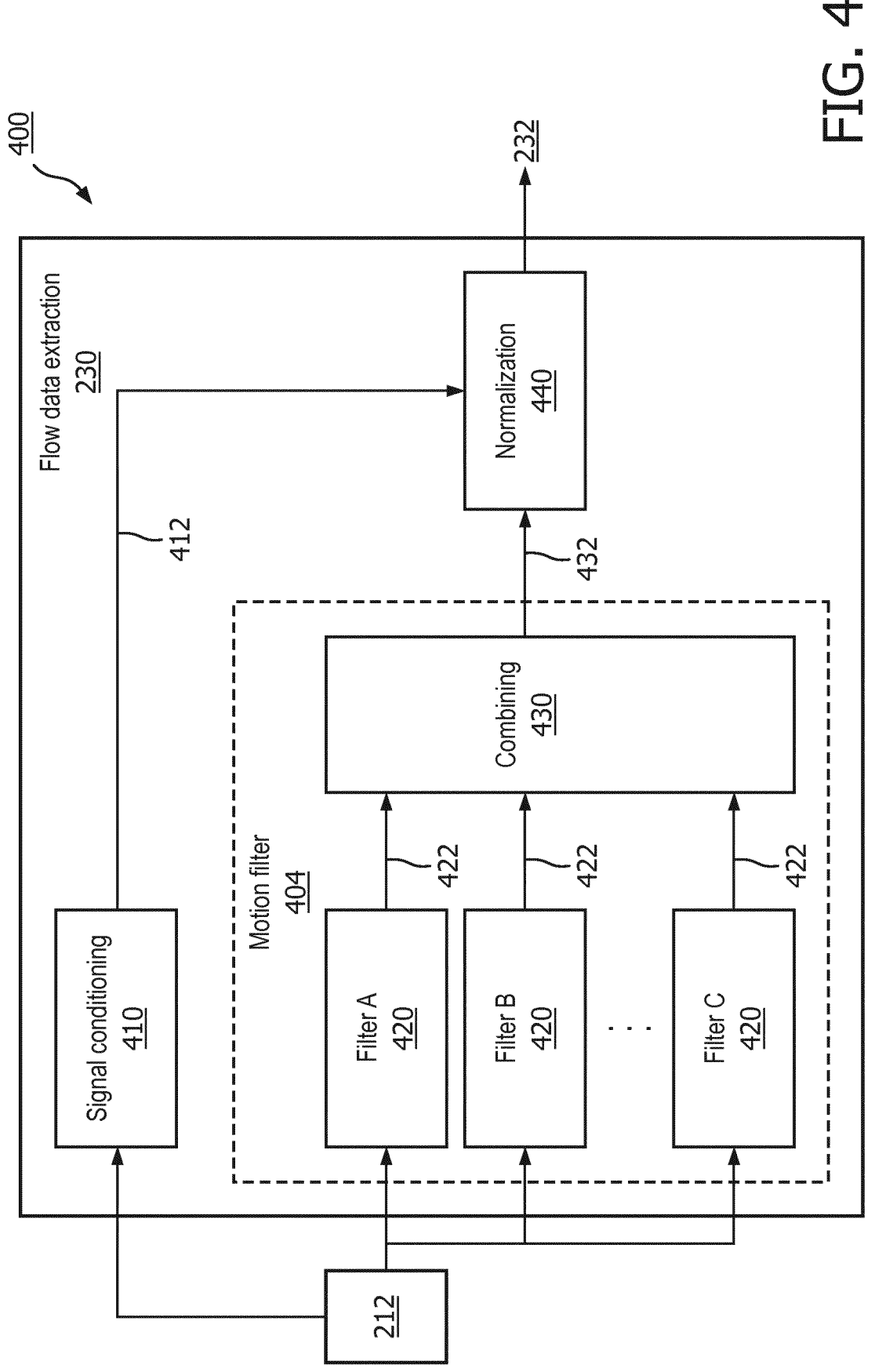
FIG. 4 is a schematic diagram illustrating an intraluminal flow data generation scheme, according to aspects of the present disclosure.

FIG. 4 is a schematic diagram illustrating an intraluminal flow data generation scheme 400 for intraluminal ultrasound imaging, according to aspects of the present disclosure. The scheme 400 can be implemented by the flow processing unit 204. The flow data extraction unit 230 includes a signal conditioning unit 410, a motion filter 404, and a normalization unit 440.

The motion filter 404 is configured to detect the fluid flow or blood flow within the body lumen. The motion filter 404 generates the decorrelation in a set of A-line signals in the ultrasound data 212 acquired by the same aperture 302 (e.g., using the same group of acoustic elements 320). The motion filter 404 may include a bank of filters 420 coupled to a combining unit 430. Each filter 420 is configured to determine flow information associated with a different flow rate. For example, each filter 420 includes a set of sinusoidal filter coefficients tuned to a flow rate of interest (e.g., matching to a certain periodicity of a blood speckle velocity). Each filter 420 is applied to the ultrasound data 212 on a per aperture 302 basis. In other words, each filter 420 is applied to a set of A-line signals acquired using the same aperture 302. Each filter 420 produces one filtered output vector 422 (e.g., an A-line signal) as described in greater detail below with respect to FIG. 5 below.

Figure 5:
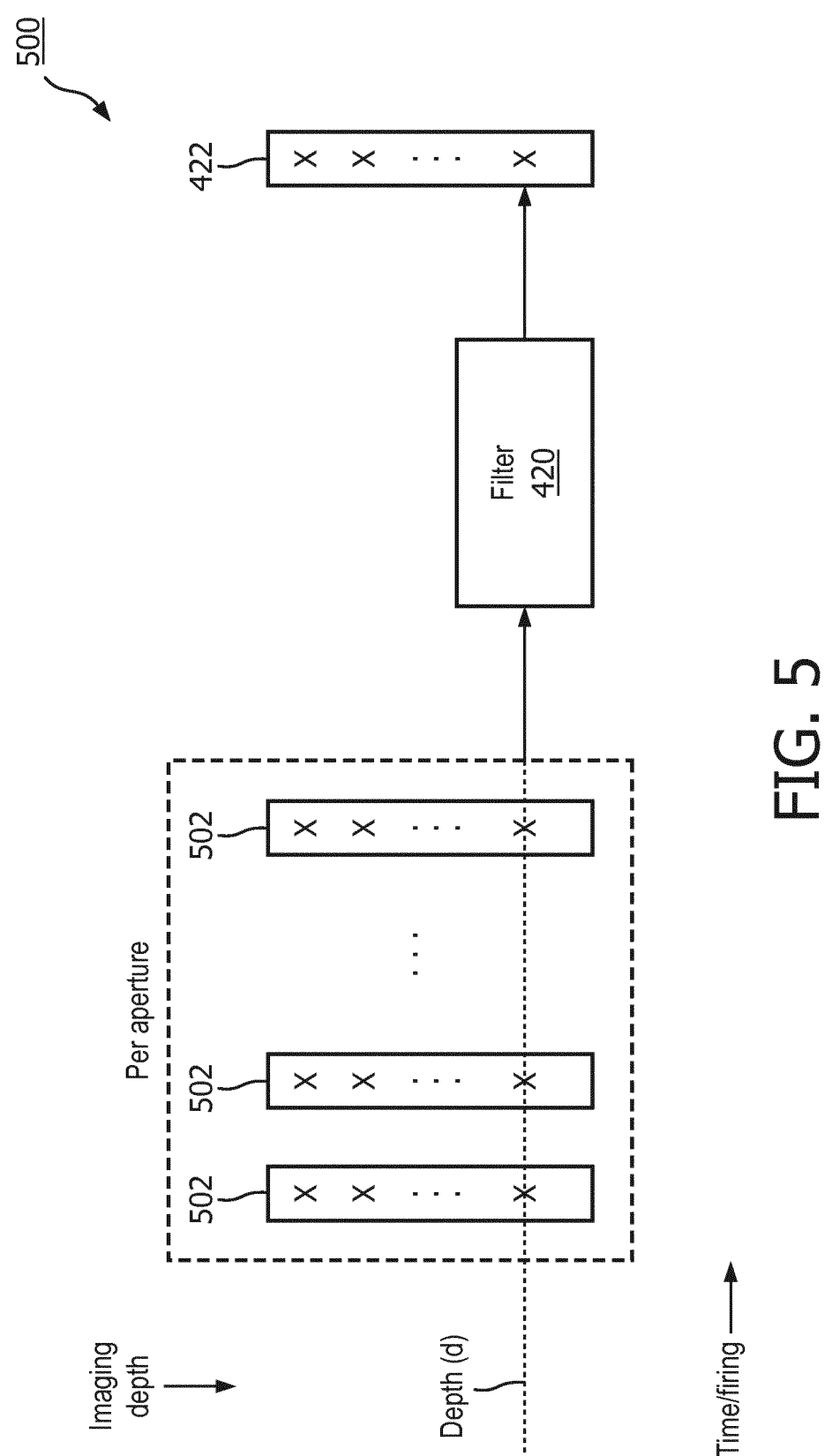
FIG. 5 is a schematic diagram illustrating a filtering scheme for intraluminal flow data generation, according to aspects of the present disclosure.

FIG. 5 is a schematic diagram illustrating a filtering scheme 500 for intraluminal flow data generation, according to aspects of the present disclosure. In the scheme 500, a set of A-line signals 502 $r$ is filtered by the filter 420 to produce an output vector 422. The set of A-line signals 502 correspond to A-line signals in the ultrasound data 212. The set of A-line signals 502 are acquired repeatedly using the same aperture 302 (e.g., the aperture 302a) over a period of time. Each A-line signal 502 may include a plurality of samples represented by the symbol X. At any imaging depth, denoted as d, the filtering operation at the filter 420 can be expressed as shown below:

$$C = A \cdot B = \sum_{i=1}^{L} a_i \times b_i,$$

where C represents a sample in the filter output 422 at the imaging depth d, L represents the length of filter taps or filter coefficients in the filter 420, $b_i$ represents the set of filter coefficients, and $a_i$ represents the samples in the set of A-lines 502 at the imaging depth d across time. In some instances, the filter tap length L may be the same as the number of A-line signals or the number of firings per aperture 302.

Returning to FIG. 4, the combining unit 430 combines the output vectors 422 output by the filters 420 for each aperture 302. Thus, the motion filter 404 generates N number of output vectors 432 (e.g., A-line signals), each corresponding to an aperture 302. The output vectors 432 can also be referred to as flow signals. In some embodiments, the motion filter 404 can be alternatively configured to include a single filtering stage instead of multiple parallel filtering stages (e.g., the bank of filters 420) as shown to achieve similar functionalities. However, the use of multiple filters 420 separately can lead to an improved SNR and a certain amount of flow fill-in (compounding). The relative echo levels from the blood flow can be more pronounced with the multiple parallel filtering stages.

While the motion filter 404 can be configured to extract motion information caused by the fluid flow in the body lumen, in some instances, certain tissue structures (e.g., due to cardiac movements) can remain in the A-line signals or output vectors 432. This is because the motion filter 404 essentially process structural information in a temporal manner, and thus the output vectors 432 is a product of motion and backscatter strength of the structures (e.g., the body lumen) moving. As such, it is similar to a power flow technique. The inclusion of tissue structures or backscatter in the output vectors 432 can result in ghost artifacts in the final flow image.

Accordingly, the present disclosure provides techniques to improve the capturing of flow information by applying a structural normalization that is backscatter intensity based so that the flow data extraction unit 230 outputs motion information only or at least with a significant reduced amount of tissue movements.

As shown, the normalization unit 440 is coupled to the signal conditioning unit 410 and the combining unit 430. The signal conditioning unit 410 is configured to apply a signal conditioning function to the ultrasound data 212. The signal conditioning function can be any suitable signal processing function. In an embodiment, the signal conditioning function includes a signal averaging function. For example, for each aperture 302, the signal conditioning unit 410 computes an average absolute signal level 412 across samples in the set of A-lines 502. In other words, the signal conditioning unit 410 produces an average signal level 412 for each imaging depth. The normalization unit 440 applies the average signal level 412 to the filtered A-lines or output vectors 432, for example, by dividing each sample in the output vectors 432 by the average signal level 412 of a corresponding depth to produce the output vectors 232. The division operation can be implemented in any suitable manner, for example, a combination of multiplication, division, and/or bit-shifting. In some instance, a lookup table (LUT) may be used to simplify the implementation of the division operations. The normalization can reduce artifacts from the strong tissue signal and amplify the flow signal, and thus improve the quality and/or clarity of the flow information.

In some embodiments, the normalization unit 440 can improve the quality of the final flow image by applying thresholding to the normalization process, for example, based on a certain noise level, to suppress noise in the flow data. For example, the normalization unit 440 may set a sample at the output vector 232 to a value of zero when the average signal level 412 at a corresponding imaging depth is below a certain level.

In some embodiments, the normalization unit 440 can further improve the quality of the final flow image by applying weightings or thresholding to the normalization process, for example, based on an imaging depth as described in greater detail below with respect to FIG. 6.

Figure 6:
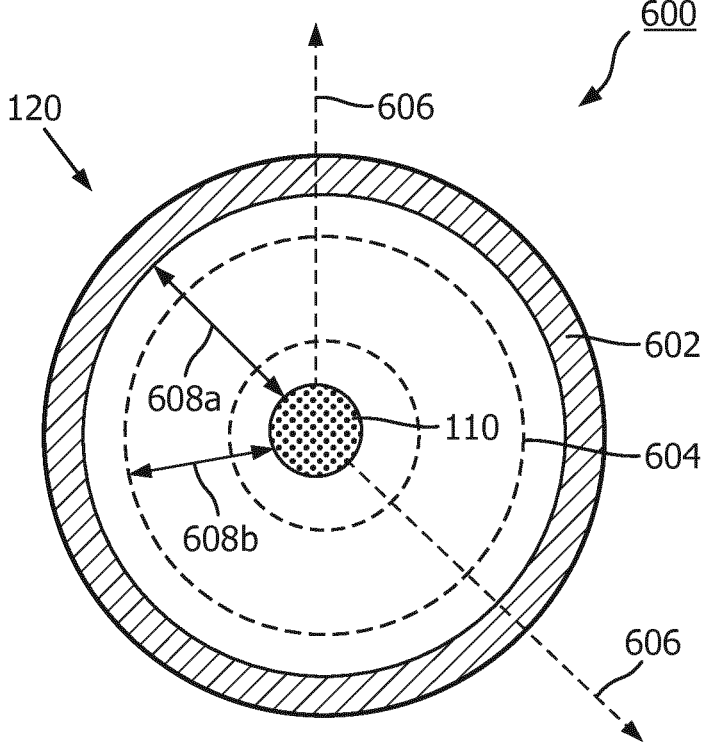
FIG. 6 is a schematic diagram illustrating a cross-sectional view of a body lumen under imaging, according to aspects of the present disclosure.

FIG. 6 is a schematic diagram illustrating a cross-sectional view 600 of a body lumen under imaging, according to aspects of the present disclosure. For example, the cross-sectional view 600 is taken along the line 150 of FIG. 1 where the imaging component 110 is located. The vessel 120 includes vessel tissues or structures 602 forming a lumen 604, where fluid or blood may flow through the lumen 604. The imaging component 110 can emit ultrasound waves to form A-line signals (e.g., the A-line signals 502) along the lines 606. The imaging depths (e.g., the depth d) may refer to the radial distance 608 extending from the imaging component 110 towards the vessel structure 602. The normalization unit 440 may normalize the flow signals or the filter output vectors 432 based on imaging depths. For example, the imaging depths may be divided into ranges as shown by the dashed circles. Different weightings may be applied to normalize motion or flow samples (e.g., in the output vectors 432) of different depths. For example, the normalization unit 440 may use different LUTs each corresponding to a different range of imaging depths and may scale the signal levels of flow samples in the output vector 432 using a LUT of a corresponding imaging depth range.

Returning to FIG. 2, the flow data extraction unit 230 generates one A-line signal or output vector 232 for each aperture 302 or 304. The flow post processing unit 240 is coupled to the flow data extraction unit 230 and configured to process the flow signals or vectors 232. The flow post processing unit 240 can apply signal conditioning functions (e.g., time-gain compensation, envelop detection, and/or filtering) to further improve the SNR of the flow signals or vectors 232. The flow post processing unit 240 can format the flow signals or vectors 232 so that the flow signals or vectors 232 are suitable for combining with the B-mode imaging data or structural data 262. The formatting may include azimuthal interpolation, log compression, and/or persistence processing. The flow post processing unit 240 produces post-processed flow data 242.

The scan conversion unit 250 is coupled to the flow post processing unit 240. The scan conversion unit 250 is substantially similar to the scan conversion unit 270. For example, the flow data 242 is in a polar coordinate system and the scan conversion unit 250 coverts the flow data 242 to a Cartesian coordinate system. The scan conversion unit 250 produces flow data 252. The flow data 252 may include pixel values in an x-y coordinate system. The pixel values are flow signal levels or flow intensities at the pixel locations in the x-y coordinate system.

The image combining unit 280 receives the scan-converted flow data 252 and the scan-converted structural data 272. The image combining unit 280 combines the flow data 252 and the structural data 272 to produce a single image frame showing fluid flow in the body lumen as described in greater detail below with respect to FIG. 7.

Figures 7, 8:
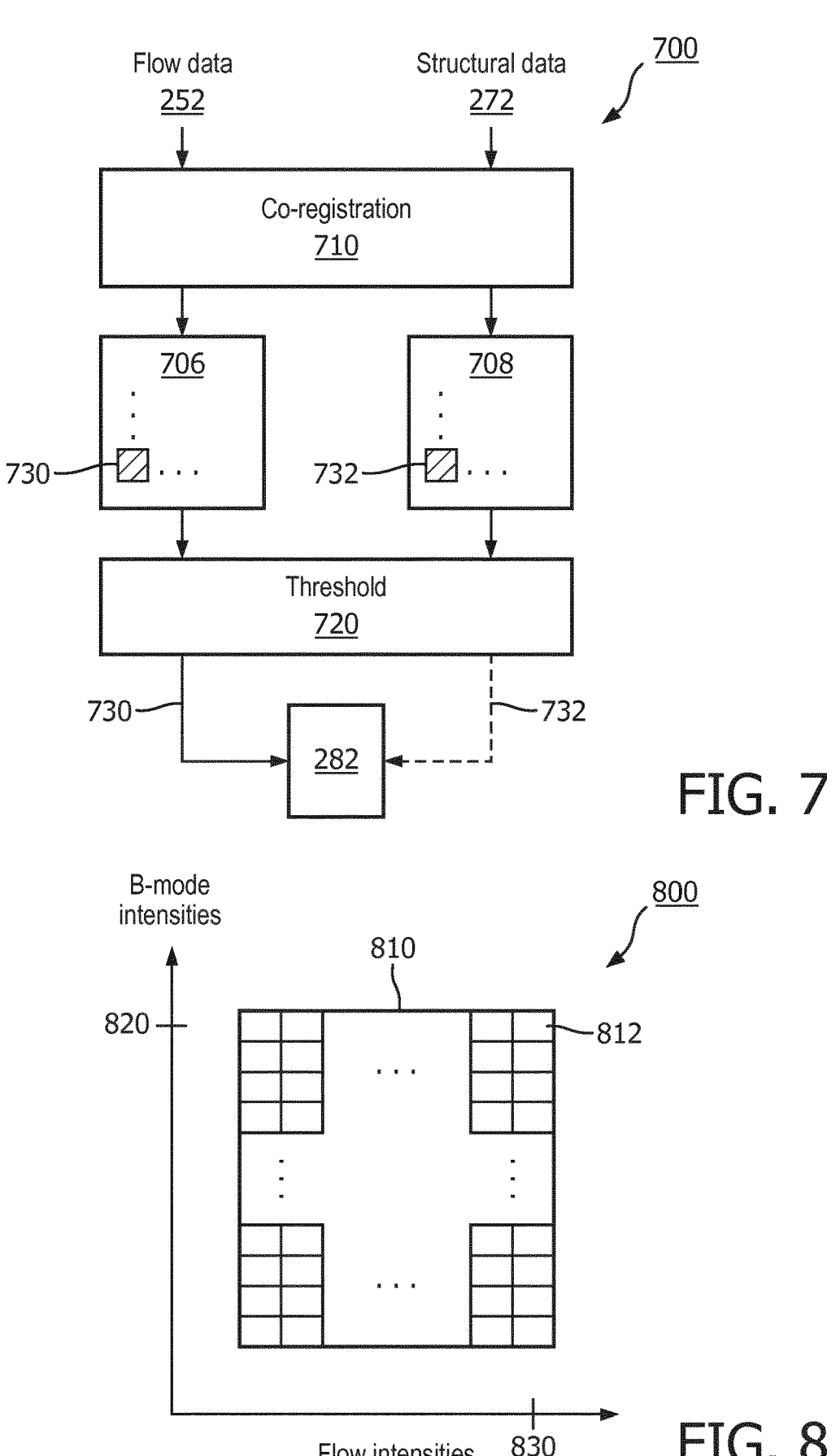
FIG. 7 is a schematic diagram illustrating an intraluminal image data combining scheme, according to aspects of the present disclosure.
FIG. 8 illustrates a color mapping scheme for displaying a flow lumen, according to aspects of the present disclosure.

FIG. 7 is a schematic diagram illustrating an intraluminal image data combining scheme 700 for intraluminal ultrasound flow imaging and B-mode imaging, according to aspects of the present disclosure. The scheme 700 is implemented by the image combining unit 280. The scheme 700 includes a B-mode/flow data co-registration unit 710 and a thresholding unit 720. The B-mode/flow data co-registration unit 710 receives the flow data 252 and the structural data 272. The B-mode/flow data co-registration unit 710 co-registers the receives the flow data 252 and the structural data 272 so that the spatial locations of the flow data 252 and the structural data 272 are in alignment. The co-registration may include orienting or rotating the flow data 252 and the structural data 272 since the flow data 252 and the structural data 272 are captured using different aperture sizes (e.g., the apertures 302 and 306). The B-mode/flow data co-registration unit 710 outputs aligned or co-registered flow data 706 and structural data 708. After the co-registration, the flow data 706 and the structural data 708 are aligned spatially with respect to the body lumen.

After the co-registration, the thresholding unit 720 is applied to the aligned flow data 706 and structural data 708. The threshold unit 720 can apply a binary logic to determine whether to select a pixel value from the flow data 706 or from the structural data 708 for display. Ideally, when a corresponding spatial location include fluid flow in the body lumen (e.g., the lumen 604), the thresholding unit 720 selects the pixel value from the flow data 706. Conversely, when a corresponding spatial location (e.g., pixel location) corresponds to structures (e.g., the structures 602) of the body lumen, the thresholding unit 720 selects the pixel value from the structural data 708. Accordingly, the present disclosure provides techniques to apply the thresholding based on the strength of the flow signal or the flow rate so that stronger flows are displayed as flow information in the final image.

The thresholding unit 720 applies the thresholding for the combining as a function of signal levels of the flow data 706. In other words, the thresholds are set by the flow intensities. For example, at each pixel location, the B-mode intensity 732 in the structural data 708 is compared to a threshold that is defined by the flow intensity 730 at a corresponding pixel location in the flow data 706. As a result, the pixel is treated as flow information if the B-mode intensity 732 is below the threshold, where the thresholding unit 720 outputs the flow intensity 730 from the flow data 706. Otherwise, the pixel is treated as B-mode information, where the thresholding unit 720 outputs the B-mode intensity 732 from the structural data 708. In an embodiment, the threshold for each flow intensity level may be predetermined. For example, a higher flow intensity level sets a higher threshold. In other words, stronger flow information or higher flow intensities are favored over the structural information for the display in the final image. After the selection or combining, the thresholding unit 720 produces an image 282 including flow information and structural information of the body lumen. The image 282 can be output to the display 108 for display. The pixels representing flow information (e.g., carrying flow intensities) can be displayed in color and the pixels representing structural information (e.g., carrying B-mode intensities) can be displayed in gray-scale.

Accordingly, the varying flow-intensity or flow-rate based thresholds can remove islands of gray B-mode structural data in a flow lumen when it is clear the data is ghost artifact from grating and side lobe clutter because the flow is quite strong in the proximity of the same area.

FIG. 8 illustrates a color mapping scheme 800 for displaying a flow lumen, according to aspects of the present disclosure. The scheme 800 is implemented by the image combining unit 280. However, instead of applying thresholding or comparison logic using the thresholding unit 720, the scheme 800 uses a LUT 810 to combine the flow data 706 and the structural data 708. The LUT 810 is a 2-dimensional LUT including flow input intensities in the x-axis and B-mode input intensities in the y-axis. The scheme 800 maps a pair of B-mode intensity 820 similar to the B-mode intensity 732 (e.g., from the structural data 708) and flow intensity 830 similar to the flow intensity 730 (e.g., from the flow data 706) into a red-green-blue (RGB) pixel 812 for display based on the LUT 810. In an embodiment, the RGB pixels 812 may represent at least about 256 colors and at least about 256 gray-scale levels. For pixels representing structural information, the values of each of the R, G, and B channels can be equal to each other to produce a gray-scale output. For pixels representing flow information, the values of the R, G, and B channels define their specific colors. The base values for each of R, G, and B channels can be linearly interpolated for smooth color representations of the 256 possible colors (e.g., chroma intensities). The RGB pixels 812 may include values of any suitable bit-length. In an embodiment, each RGB pixel 812 includes a value of about 24 bits in length.

The scheme 200 illustrates various mechanisms for reducing ghost artifacts from tissues or structures being included in the flow information of the final image 282. An intraluminal imaging system (e.g., the system 100) may apply any suitable combinations of the mechanisms described above including the normalization of the output (e.g., the output vectors 432) of the motion filter 404, the range-based or imaging depth-based normalizations, and the flow rate-based thresholding or the flow rate-based LUT 810 in the combining of the flow data 706 and structural data 708.

FIG. 9 is a flow diagram of an intraluminal ultrasound image generation method 900, according to aspects of the disclosure. Steps of the method 900 can be executed by the system 100. The method 900 may employ similar mechanisms as in the schemes 200, 300, 400, 500, 700, and 800 as described with respect to FIGS. 2, 3, 4, 5, 7, and 8, respectively. As illustrated, the method 900 includes a number of enumerated steps, but embodiments of the method 900 may include additional steps before, after, and in between the enumerated steps. In some embodiments, one or more of the enumerated steps may be omitted or performed in a different order.

At step 910, the method 900 includes receiving first A-line signal data (e.g., the ultrasound data 212) and second A-line signal data (e.g., the ultrasound data 222) associated with a body lumen (e.g., the vessel 120 and the target 310) of a patient, for example, from the intraluminal imaging device 102. The first A-line signal data and the second A-line signal data are acquired by the imaging component 110 configured with different imaging mode configurations, for example, using the flow imaging configuration unit 210 and the B-mode imaging configuration unit 220. In general, the first and second A-line signal data may be ultrasound data representing any anatomy and/or any anatomical structure.

The first A-line signal data and the second A-line signal data can be acquired in any suitable order. In an example, the first A-line signal data and the second A-line signal data are acquired in an order of the A-lines. In other words, the first A-line signal data and the second A-line signal data are acquired A-line-by-A-line. In some instances, A-lines of the first A-line signal data may interleave with A-lines of the second A-line signal data. In another example, the first A-line signal data and the second A-line signal data are acquired in an order based on an imaging depth. In other words, samples of the first A-line signal data and/or the second A-line signal data at a first imaging depth are acquired followed by samples of the first A-line signal data and/or the second A-line signal data at a next imaging depth.

At step 920, the method 900 includes generating intraluminal flow data (e.g., the flow data 706) from the first A-line signal data, for example, by applying the motion filter 404 to the first A-line signal data. For example, the intraluminal motion data includes flow intensities representing the fluid flow within the body lumen.

At step 930, the method 900 includes normalizing the intraluminal flow data by applying a scaling function to the intraluminal flow data based on signals levels of the first A-line signal data, for example, using the normalization unit 440.

At step 940, the method 900 includes generating intraluminal structural data (e.g., the structural data 708) from the second A-line signal data, for example, by using the B-mode processing unit 260. For example, the intraluminal structural data includes B-mode intensities representing the tissue structures (e.g., the structures 602) of the body lumen.

At step 950, the method 900 includes combining the intraluminal flow data and the intraluminal structural data based on a first threshold associated with signal levels of the intraluminal flow data to produce an intraluminal ultrasound image (e.g., the image 282), for example, using the image combining unit 280.

At step 960, the method 900 includes displaying the intraluminal image, for example, on the display 108.

In an embodiment, the normalization is based on an average signal level (e.g., the average signal level 412) of the first A-line signal data. In an embodiment, the normalization includes applying a second threshold to the average signal level of the first A-line signal data, the second threshold associated with a noise level of the first A-line signal data. In an embodiment, the normalization is based on an imaging depth, for example, the radial distance (e.g., the radial distances 608) between the ultrasound transducer array and the location corresponding to the samples in the first A-line signal data.

In an embodiment, the combining includes determining whether to assign a first flow intensity (e.g., the flow intensity 730) of the flow intensities in the motion data or a first B-mode intensity (e.g., the B-mode intensity 732) of the B-mode intensities in the structural data to the combined motion data and structural data based on the first threshold, for example, using the thresholding unit 720. The combining includes assigning the first B-mode intensity to the combined motion data and structural data when the first B-mode intensity exceeds the first threshold. The combining includes assigning the first flow intensity to the combined motion data and structural data when the first B-mode intensity is equal to or below the first threshold. The first threshold is a function of the first flow intensity.

In an embodiment, the combining is based on a LUT (e.g., the LUT 810) including flow intensities and B-mode intensities configured based on the first threshold. The combining includes selecting a value (e.g., the RGB pixels 812) from the LUT based on a first flow intensity (e.g., the flow intensity 830) of the flow intensities in the motion data, a first B-mode intensity (e.g., the B-mode intensity 820) of the B-mode intensities in the structural data, and a co-registration between the motion data and the structural data and assigning the selected value to the combined motion data and structural data.

In an embodiment, the displaying includes displaying a first region of the intraluminal ultrasound image corresponding to the intraluminal motion data in a first palette and displaying a second region of the intraluminal ultrasound image corresponding to the intraluminal structural data in a second palette different from the first palette. In an example, the first palette may be in color and the second palette may be in gray-scale. In an example, the first palette may be in gray-scale and the second palette may be in color. In an example, the first palette and the second palette may include different sets of colors.

Aspects of the present disclosure can provide several benefits. For example, the normalization of the motion filter output can reduce the likelihoods of including moving tissues (e.g., caused by the cardiac cycle of a patient) in the fluid or flow motion, and thus reducing artifacts in the final image at the regions corresponding to the flow information. The flow-rate based or flow signal level-based thresholding in the combining of the motion data and B-mode data increases the likelihoods for displaying flow information when stronger flows are present. Thus, the normalization and the flow-rate based or flow signal level-based thresholding can reduce or remove ghost artifacts (e.g., islands of gray scale B-mode structural data) from areas in a flow lumen corresponding to fluid flow.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An ultrasound imaging system, comprising:
an intravascular imaging catheter comprising:
  a flexible elongate member configured to be positioned within a blood vessel of a patient heart; and
  a circumferential ultrasound transducer array coupled to the flexible elongate member, wherein the ultrasound transducer array is configured to obtain first signal data and second signal data associated with different imaging modes; and
a processor configured for communication with the intravascular imaging catheter, and wherein the processor is configured to:
  generate, based on the first signal data, motion data representative of first motion and second motion, wherein the first motion is blood flow motion and the second motion is tissue motion, wherein the motion data comprises a plurality of vectors spatially distributed around the circumferential ultrasound transducer array, wherein each vector of the plurality of vectors comprises a plurality of samples representing a plurality of imaging depths away from the ultrasound transducer array;

distinguish between the first motion and the second motion, wherein, to perform the distinguishing, the processor is configured to:
  determine, based on the first signal data, a respective average signal level for each imaging depth of the plurality of imaging depths; and
  apply the respective average signal level to each sample at a corresponding imaging depth in the plurality of vectors;
generate structural data based on the second signal data, wherein the structural data represents the blood vessel;
combine the motion data and the structural data to determine motion pixels and structure pixels forming an intravascular image, wherein the distinguishing and the determination of the motion pixels and structure pixels are distinct from one another; and
output the intravascular image to a display in communication with the processor.

2. The system of claim 1,
wherein the processor is configured to apply a noise threshold to the respective average signal level,
wherein the noise threshold is associated with a noise level of the first signal data.

3. The system of claim 1, wherein the processor is configured to normalize the motion data by applying a scaling function to the motion data based on the corresponding imaging depth.

4. The system of claim 1,
wherein the motion data includes flow intensities,
wherein the structural data includes B-mode intensities,
wherein the processor is configured to combine the motion data and the structural data by:
  determining whether to assign a first flow intensity of the flow intensities in the motion data or a first B-mode intensity of the B-mode intensities in the structural data to the combined motion data and structural data based on an intensity threshold.

5. The system of claim 4, wherein the processor is configured to combine the motion data and the structural data by:
  assigning the first B-mode intensity to the combined motion data and structural data when the first B-mode intensity exceeds the intensity threshold.

6. The system of claim 4, wherein the processor is configured to combine the motion data and the structural data by:
  assigning the first flow intensity to the combined motion data and structural data when the first B-mode intensity is equal to or below the intensity threshold.

7. The system of claim 4, wherein the intensity threshold varies as a function of the first flow intensity.

8. The system of claim 4,
wherein the motion data includes flow intensities,
wherein the structural data includes B-mode intensities,
wherein the processor is configured to combine the motion data and the structural data by:
  selecting a value from a lookup table based on a first flow intensity of the flow intensities in the motion data, a first B-mode intensity of the B-mode intensities in the structural data, and a co-registration between the motion data and the structural data, the lookup table including B-mode intensities and flow intensities associated with the intensity threshold; and
  assigning the selected value to the combined motion data and structural data.

9. The system of claim 8, wherein the flow intensities in the lookup table includes at least 256 flow intensity levels.

10. The system of claim 4, wherein the processor is configured to:

compute the intensity threshold comprising a value that varies according to values of intensities that are present during intravascular imaging.

11. The system of claim 1, wherein the circumferential ultrasound transducer array comprises a plurality of acoustic elements arranged around a longitudinal axis of the flexible elongate member, wherein the first signal data is acquired based on a first imaging mode configured with an aperture including a first quantity of the plurality of acoustic elements, and wherein the second signal data is acquired based on a second imaging mode configured with an aperture including a second quantity of the plurality of acoustic elements different from the first quantity.

12. The system of claim 1, further comprising:

the display configured to display the intravascular image by:

displaying a first region of the intravascular image associated with the motion data in color; and displaying a second region of the intravascular image associated with the structural data in gray-scale.

13. The system of claim 1, wherein the motion data comprise at least one of flow intensities, color intensities, or chroma intensities, and wherein the structural data comprise at least one of B-mode intensities, gray-scale intensities, or brightness intensities.

14. A method of ultrasound imaging, comprising:

receiving first signal data and second signal data representative of a blood vessel of a patient heart during intravascular imaging, wherein the first signal data and the second signal data are acquired from a circumferential ultrasound transducer array of an intravascular imaging catheter and coupled to a flexible elongate member positioned within the blood vessel, wherein the first signal data and the second signal data are associated with different imaging modes;

generating, based on the first signal data, motion data representative of first motion and second motion, wherein the first motion is blood flow motion and the second motion is tissue motion, wherein the motion data comprises a plurality of vectors spatially distributed around the circumferential ultrasound transducer array, wherein each vector of the plurality of vectors comprises a plurality of samples representing a plurality of imaging depths away from the ultrasound transducer array;

distinguish between the first motion and the second motion, wherein the distinguishing comprises:

determining, based on the first signal data, a respective average signal level for each imaging depth of the plurality of imaging depths; and applying the respective average signal level to each sample at a corresponding imaging depth in the plurality of vectors;

generating structural data based on the second signal data, wherein the structural data represents the blood vessel;

combining the motion data and the structural data to determine motion pixels and structure pixels forming an intravascular image, wherein the distinguishing and the determination of the motion pixels and structure pixels are distinct from one another; and outputting, to a display, the intravascular image.

* * * * *